United States Patent [19]

Scholz

[11] 4,168,279

[45] Sep. 18, 1979

[54] MANUFACTURE OF AMINES OF THE FORMULA AR—NH—CH$_2$—R

[75] Inventor: Herbert Scholz, Ludwigshafen, Fed. Rep. of Germany

[73] Assignee: BASF Aktiengesellschaft, Fed. Rep. of Germany

[21] Appl. No.: 839,776

[22] Filed: Oct. 6, 1977

[30] Foreign Application Priority Data

Nov. 2, 1976 [DE] Fed. Rep. of Germany ....... 2650232

[51] Int. Cl.$^2$ ..................... C07C 85/11; C07C 85/147
[52] U.S. Cl. ...................... 260/573; 536/18; 536/53
[58] Field of Search .............. 260/573; 536/53, 18

[56] References Cited

U.S. PATENT DOCUMENTS

| | | | |
|---|---|---|---|
| 2,193,433 | 3/1940 | Salzberg | 260/573 |
| 2,411,611 | 11/1946 | Bergel et al. | 536/15 |
| 2,422,997 | 6/1947 | Wuest | 536/18 |
| 4,060,551 | 11/1977 | Uchikuga et al. | 260/561 S |

FOREIGN PATENT DOCUMENTS 1342020 12/1973 United Kingdom ..................... 260/581

OTHER PUBLICATIONS

Jampolsky et al., "J. Amer. Chem. Soc.", vol. 68, pp. 1777-1778 (1946).
Adams, "Organic Reactions", vol. 8, p. 7 (1954).

*Primary Examiner*—Patrick Garvin
*Assistant Examiner*—John Doll
*Attorney, Agent, or Firm*—Keil & Witherspoon

[57] ABSTRACT

Amines of the formula Ar—NH—CH$_2$—R, where Ar is unsubstituted or substituted phenyl and R is alkyl of 3 to 6 carbon atoms substituted by hydroxyl groups, are manufactured by catalytic hydrogenation of a salt of an acid of the formula R—COOH in the presence of (a) a compound of the formula Ar—Z, where Z is a nitro or reduced nitro group, and a strong acid or (b) a salt of an amine of the formula Ar—NH$_2$ and a strong acid, in an organic solvent.

12 Claims, No Drawings

MANUFACTURE OF AMINES OF THE FORMULA AR—NH—CH₂—R

The present invention relates to a new process for the manufacture of amines which are used, for example, as valuable intermediates for the manufacture of drugs. For example, N-[3,4-dimethylphenyl]-N-D-ribamine of the formula V

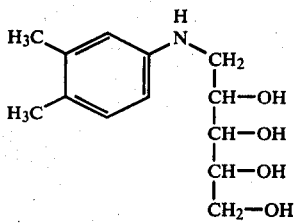

an industrial key product for the manufacture of vitamin B 2, may be manufactured particularly advantageously by the process of the invention.

The conventional process of manufacture of N-[3,4-dimethylphenyl]-N-D-ribamine involves the stages D-glucose→potassium arabonate→calcium arabonate→calcium ribonate→D-ribonic acid γ-lactone→D-ribose→N-[3,4-dimethylphenyl]-N-D-ribamine (see J. Fragner, Vitamine, Volume II, G. Fischer Verlag Jena 1965, page 1381), and it is an object of the invention to provide a process whereby this important vitamin intermediate can be manufactured in an advantageous manner.

I have found that this object is achieved and that amines of the formula I

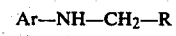

where Ar is phenyl which is unsubstituted or substituted by alkyl, alkoxy and/or halogen and R is alkyl of 3 to 6 carbon atoms substituted by hydroxyl groups can be manufactured particularly advantageously by catalytic hydrogenation of a salt of an acid of the formula R—COOH (II) in the presence of
(a) a compound of the formula III

where Z is nitro or reduced nitro, and a strong acid, or
(b) a salt of an amine of the formula Ar-NH₂ and a strong acid, in an organic solvent.

The acids of the formula R—COOH are preferably aldonic acids of 4 to 7 carbon atoms which may be in the D, L or DL configuration. Examples are gluconic acid, mannonic acid, gulonic acid, galactonic acid, allonic acid, altronic acid, heptonic acid, ribonic acid, arabonic acid, xylonic acid, lyxonic acid, erythronic acid and threonic acid. Amongst these aldonic acids, D-ribonic acid, D-arabonic acid and D-gluconic acid are of particular industrial interest. The said acids are employed as salts, preferably as metal salts in which the metal may be an alkali metal, eg. sodium or potassium, an alkaline earth metal, eg. calcium or barium, a transition metal, eg. iron, or another metal, eg. lead or cadmium. The cation of the aldonic acid salt may however also be an unsubstituted or substituted ammonium ion. The sodium and potassium salts are preferred.

The aromatic radical Ar present in the aromatic starting materials of the formula Ar—Z (III) is phenyl which may be unsubstituted or substituted by alkyl, alkoxy and/or halogen. Alkyl and alkoxy is, for example, of 1 to 4 carbon atoms. Examples of substituents are methyl, ethyl, propyl, butyl, methoxy, ethoxy, chlorine and bromine. The phenyl radical may also contain a plurality of the said substituents, eg. from two to four. Z is nitro or reduced nitro; examples of the latter are amino, azoxy, azo, hydrazo, nitroso, hydroxylamino or diazoamino.

Examples of starting materials of the formula III are compounds of the formula IV

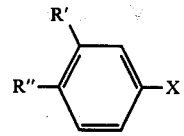

where R' and R" are hydrogen or methyl, X is —NH₂, NO₂, —NO, —NHOH, —NH—N=N—R''', —NH—NH—R''' or —NO—N—R''' and R''' is phenyl which may be substituted by methyl in the 3- and/or 4-position.

Examples of starting materials of the general formula IV are aniline, 3,4-dimethylaniline, nitrobenzene, 3,4-dimethylnitrobenzene, 3,4,3',4'-tetramethylazoxybenzene, 3,4,3',4'-tetramethylazobenzene, 3,4,3',4'-tetramethylhydrazobenzene, 3,4-dimethylnitrosobenzene, 3,4,3',4'-tetramethyldiazoaminobenzene and 4-hydroxylamino-o-xylene. Amongst these compounds, aniline, 3,4-dimethylaniline, 3,4,3',4'-tetramethylazoxybenzene and 3,4-dimethylnitrobenzene are preferred.

Suitable strong acids are sulfuric acid and aromatic sulfonic acids.

Suitable organic solvents are conventional organic solvents which undergo little or no change under the catalytic hydrogenation conditions. Examples are alcohols, eg. methanol, ethanol, propanol and butanol, or ethers, eg. dioxane, the latter being the preferred solvent.

Examples of catalysts which may be used for the catalytic hydrogenation are metals from amongst the transition elements, eg. copper, chromium, nickel, iron, platinum, palladium, rhodium, cerium, thorium and zinc, the metals aluminum and magnesium or the oxides of the said metals. Mixtures of the said metals or metal oxides, for example the mixed oxides described in Schwab: "Handbuch der Katalyse", Volume 5, pages 567–577, are also very suitable. Copper oxide and/or copper-containing catalysts, especially those which contain finely divided copper oxide and/or copper on a catalyst carrier, have proved particularly advantageous. Examples of carriers present in these catalysts are refractory oxides, eg. chromium oxide, aluminum oxide or cerium oxide. Such catalysts are described, for example, by H. Adkins in Organic Reactions, Volume VIII, 1954, pages 8 and 9 and in German Laid-Open Application DOS No. 2,024,282. Amongst these catalysts, those containing copper oxide and chromium oxide and those containing copper oxide and aluminum oxide are very suitable.

It is particularly advantageous to treat the catalysts with hydrogen before they are used. This prehydrogenation is carried out at, for example, up to 400° C., preferably at from 150° to 250° C. and under a hydrogen pressure of from 0.01 bar (in the absence of a solvent) to 300 bars (in the case of a suspension in a solvent).

The hydrogenation according to the invention is generally carried out at from 5° to 155° C., preferably from 125° to 145° C. The hydrogen pressure is generally from 1 to 1,000 bars, preferably from 100 to 300 bars. Advantageously, the starting materials are reacted in the stoichiometric ratio. Advantageously, from 100 to 400 parts by weight of solvent are used per 100 parts by weight of the mixture of the starting materials.

The amines of the formula I are obtained in good yield by the process of the invention. N-[3,4-dimethylphenyl]-N-D-ribamine thus obtained is converted into vitamin $B_2$ by the methods described in J. Fragner, Vitamine, Volume II, G. Fischer Verlag Jena 1965, page 1381.

EXAMPLE 1

A suspension of 34.0 g (0.1 mole) of 3,4-dimethylaniline sulfate and 40.8 g (0.2 mole) of potassium D-ribonate in 100 ml of dioxane is hydrogenated with 18 g of a copper oxide/aluminum oxide catalyst (which has been prehydrogenated in 50 ml of dioxane for 8 hours at 200° C. under 150 bars hydrogen pressure) for 24 hours at 145° C. under an initial pressure of 300 bars of hydrogen in a stirred rotary autoclave, with the stirrer running at 250 revolutions per minute. After the hydrogenation has ended, 200 ml of methanol are added, the mixture is heated, the catalyst and the potassium sulfate formed are filtered off, the filtrate is concentrated and the residue is recrystallized from methanol.

Yield: 60% of N-[3,4-dimethylphenyl]-N-D-ribamine.

The IR spectrum agrees with the structure of N-[3,4-dimethylphenyl]-N-D-ribamine.

EXAMPLE 2

9.81 g (0.1 mole) of concentrated sulfuric acid are added to a suspension of 40.8 g (0.2 mole) of potassium -D-ribonate in 100 ml of dioxane. 24.2 g (0.2 mole) of 3,4-dimethylaniline and 18 g of the prehydrogenated copper oxide/aluminum oxide catalyst described in Example 1 are added. The hydrogenation at 135° C. under an initial hydrogen pressure of 300 bars lasts 24 hours.

The mixture is worked up as described in Example 1.
Yield: 65% of N-[3,4-dimethylphenyl]-N-D-ribamine.

EXAMPLE 3

The procedure described in Example 2 is followed, but instead of 0.2 mole of 3,4-dimethylaniline, 30.3 g (0.2 mole) of 3,4-dimethylnitrobenzene are employed. N-[3,4-Dimethylphenyl]-N-D-ribamine is obtained in a yield which is somewhat less than that obtained by the method described in Example 2.

EXAMPLE 4

9.8 g of oleum which contains 24% of $SO_3$ are added dropwise, whilst cooling with ice, to a suspension of 40.8 g (0.2 mole) of potassium D-ribonate in 80 ml of dioxane, and 24.2 g (0.2 mole) of 3,4-dimethylaniline are added. The hydrogenation and working-up are carried out as described in Example 2.

Yield: 60% of N-[3,4-dimethylphenyl]-N-D-ribamine.

EXAMPLE 5

A suspension of 37 g (0.1 mole) of calcium D-ribonate in 80 ml of dioxane is mixed with 5.4 ml (0.1 mole) of concentrated sulfuric acid and 24.4 g (0.2 mole) of 3,4-dimethylaniline and is hydrogenated with 18 g of a Cu/Al/mannaseite catalyst (which has been prehydrogenated in 70 ml of dioxane for 8 hours at 200° C. under 150 bars hydrogen pressure) for 24 hours at 145° C. under 300 bars hydrogen pressure. The reaction mixture is suspended in 250 ml of hot ethanol and the catalyst and calcium sulfate are then filtered off. The filtrate is concentrated and the residue is recrystallized from 150 ml of hot ethanol.

Yield: 50% of N-[3,4-dimethylphenyl]-N-D-ribamine.

EXAMPLE 6

43.6 g (0.2 mole) of sodium D-gluconate are suspended in 150 ml of dioxane and hydrogenated with 5.47 ml (0.1 mole) of concentrated sulfuric acid and 24.2 g (0.2 mole) of aniline over 18 g of a prehydrogenated copper oxide/aluminum oxide catalyst for 24 hours under 300 bars hydrogen pressure. The mixture is worked up as described in Example 5.

50% of N-phenyl-N-D-glucamine of melting point 134° C. are obtained.

I claim:
1. A process for the manufacture of an amine of the formula I

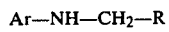

Ar—NH—CH$_2$—R     I where Ar is phenyl which is unsubstituted or substituted by at least one radical selected from the group consisting of alkyl, alkoxy and halogen and R is alkyl of 3 to 6 carbon atoms substituted by hydroxyl groups which comprises:

catalytically hydrogenating a salt of an acid of the formula RCOOH (II) in the presence of an effective amount of a catalyst containing copper oxide, copper or mixtures thereof in an organic solvent and in the presence of a strong acid and a compound of the formula III

Ar—Z     III where Z is nitro or reduced nitro at temperatures of from 125° to 145° C.

2. A process as set forth in claim 1, in which a salt of an aldonic acid of 4 to 7 carbon atoms is used as the salt of an acid of the formula II.

3. A process as set forth in claim 1, in which a salt of D-ribonic acid or of D-arabonic acid is used as the salt of an acid of the formula II.

4. A process as set forth in claim 1, in which the strong acid is sulfuric acid or aromatic sulfonic acids.

5. A process as set forth in claim 1, in which the alkyl and alkoxy contain from 1 to 4 carbon atoms.

6. A process as set forth in claim 1, in which aniline, 3,4,3',4'-tetramethylazoxybenzene, 3,4-dimethylaniline or 3,4-dimethylnitrobenzene is used as the compound of the formula III.

7. A process for the manufacture of an amine of the formula I

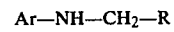

Ar—NH—CH$_2$—R     I where Ar is phenyl which is unsubstituted or substituted by at least one radical selected from the group consisting of alkyl, alkoxy and halogen and R is alkyl of 3 to 6 carbon atoms substituted by hydroxyl groups which comprises:

catalytically hydrogenating a salt of an acid of the formula RCOOH (II) in the presence of an effective amount of a catalyst containing copper oxide, copper or mixtures thereof in an organic solvent and in the presence of a strong acid and a salt of an amine of the formula Ar—NH$_2$ at temperatures of from 125° to 145° C.

8. A process as set forth in claim 7, in which a salt of an aldonic acid of 4 to 7 carbon atoms is used as the salt of an acid of the formula II.

9. A process as set forth in claim 7, in which a salt of D-ribonic acid or of D-arabonic acid is used as the salt of an acid of the formula II.

10. A process as set forth in claim 7, in which the strong acid is sulfuric acid or aromatic sulfonic acids.

11. A process as set forth in claim 7, in which the alkyl and alkoxy contain from 1 to 4 carbon atoms.

12. A process as set forth in claim 7, in which 3,4-dimethylaniline sulfate is used as the amine salt.

* * * * *